(12) United States Patent
Bobadilla et al.

(10) Patent No.: US 10,274,502 B2
(45) Date of Patent: Apr. 30, 2019

(54) BIOMARKERS AND METHODS FOR PROGRESSION PREDICTION FOR CHRONIC KIDNEY DISEASE

(71) Applicant: THE REGENTS OF THE UNIVERSITY OF MICHIGAN, Ann Arbor, MI (US)

(72) Inventors: Maria Bobadilla, Rosenau (FR); Laura Badi, Basel (CH); Guillemette Duchateau-Nguyen, Riedisheim (FR); Laurent Essioux, Attenschwiller (FR); Hanno Langen, Loerrach (DE); Maria Chiara Magnone, Basel (CH); Thomas Schindler, Loerrach (DE); Martina Thier, Basel (CH); Ivan Formentini, Basel (CH); Gonzalo Christian Duran Pacheco, Riehen (CH); Corinne Solier, Sierentz (FR); Matthias Kretzler, Ann Arbor, MI (US); Viji Nair, Ann Arbor, MI (US); Ju Wenju, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/034,338

(22) PCT Filed: Oct. 31, 2014

(86) PCT No.: PCT/EP2014/073413
§ 371 (c)(1),
(2) Date: May 4, 2016

(87) PCT Pub. No.: WO2015/063248
PCT Pub. Date: May 7, 2015

(65) Prior Publication Data
US 2016/0320410 A1    Nov. 3, 2016

(30) Foreign Application Priority Data

Nov. 4, 2013 (EP) ..................................... 13191345

(51) Int. Cl.
*G01N 33/68*    (2006.01)

(52) U.S. Cl.
CPC ..... *G01N 33/6893* (2013.01); *G01N 2333/47* (2013.01); *G01N 2333/485* (2013.01);
(Continued)

(58) Field of Classification Search
CPC .................................................. G01N 2800/52
See application file for complete search history.

(56) References Cited

U.S. PATENT DOCUMENTS

| 4,016,043 | A | 4/1977 | Schuurs et al. |
| 4,018,653 | A | 4/1977 | Mennen et al. |

(Continued)

FOREIGN PATENT DOCUMENTS

| CN | 1026522611 A | 8/2012 |
| EP | 0648228 | 4/1995 |

(Continued)

OTHER PUBLICATIONS

NKDEP—Urine Albumin to creatinine ratio, Mar. 2010.*

(Continued)

*Primary Examiner* — San Ming R Hui
(74) *Attorney, Agent, or Firm* — Casimir Jones, S.C.; Tanya Arenson

(57) ABSTRACT

Subject of the present invention are biomarkers and methods for the identification of an increased risk of the progression of chronic kidney disease (CKD), or for monitoring chronic (Continued)

kidney disease therapy, comprising the detecting the level of one or more of NTpro BNP, EGF, Apo H, GDF-15, and albumin-to-creatinine ratio.

6 Claims, 8 Drawing Sheets

Specification includes a Sequence Listing.

(52) U.S. Cl.
CPC ... *G01N 2333/495* (2013.01); *G01N 2333/58* (2013.01); *G01N 2800/347* (2013.01); *G01N 2800/52* (2013.01)

(56) References Cited

U.S. PATENT DOCUMENTS

| | | |
|---|---|---|
| 4,424,279 A | 1/1984 | Bohn et al. |
| 5,744,305 A | 4/1998 | Fodor et al. |

FOREIGN PATENT DOCUMENTS

| | | | |
|---|---|---|---|
| EP | 2336784 A1 | 6/2011 | |
| EP | 2388594 A1 | 11/2011 | |
| WO | 1993024531 | 12/1993 | |
| WO | 199906445 | 2/1999 | |
| WO | 200070051 | 11/2000 | |
| WO | 2002089657 | 10/2002 | |
| WO | 2002083913 | 11/2002 | |
| WO | 2005113585 | 12/2005 | |
| WO | 2010048670 A1 | 5/2010 | |
| WO | 2010059996 A1 | 5/2010 | |
| WO | 2011133794 A1 | 10/2011 | |
| WO | 2015063248 A2 | 5/2015 | |

OTHER PUBLICATIONS

Wynand et al., Hypertension, 2008;52:987-993.*
Snively et al., Am Fam Physician, 2004;70(10):1921-1928.*
Lapsley et al., J Clin Pathol, 1991;44:812-816.*
International Search Report of related PCT/EP2014/073413, dated Jul. 2, 2015, 7 pages.
Austin et al., "Correlation and prognostic utility of B-type natriuretic peptide and its amino-terminal fragment in patients with chronic kidney disease." Am J Clin Pathol. Oct. 2006;126(4):506-12.
Breit et al., "Macrophage inhibitory cytokine-1 (MIC-1/GDF15) and mortality in end-stage renal disease." Nephrol Dial Transplant. Jan. 2012;27(1):70-5.
Clark et al., "Dipstick proteinuria as a screening strategy to identify rapid renal decline." J Am Soc Nephrol. Sep. 2011;22(9):1729-36.
Coresh et al., "Prevalence of chronic kidney disease and decreased kidney function in the adult US population: Third National Health and Nutrition Examination Survey." Am J Kidney Dis. Jan. 2003;41(1):1-12.
Cox et al., "Regression Models and Life-Tables" Journal of the Royal Statistical Society. Series B (Methodological) vol. 34, No. 2 (1972), pp. 187-220.
Desai et al., "Association between cardiac biomarkers and the development of ESRD in patients with type 2 diabetes mellitus, anemia, and CKD." Am J Kidney Dis. Nov. 2011;58(5):717-28.
Dowdy, S., S. Wearden, and D. Chilko. "Statistics for Research. A John Wiley & Sons." Inc. publication 204 (2004): 210.
Echouffo-Tcheugui et al., "Risk models to predict chronic kidney disease and its progression: a systematic review."PLoS Med. 2012;9(11):e1001344.
Flynn et al., "Absence of increased urinary excretion of adenosine-deaminase-binding protein by patients with chronic renal tubular malfunction." Clin Chim Acta. Aug. 30, 1991;200(2-3)183-9.
Flynn et al., "Urinary excretion of beta 2-glycoprotein-1 (apolipoprotein H) and other markers of tubular malfunction in "non-tubular" renal disease." J Clin Pathol. Jul. 1992;45(7):561-7.

Formentini et al., "Current drug development challenges in chronic kidney disease (CKD)—identification of individualized determinants of renal progression and premature cardiovascular disease (CVD)." Nephrol Dial Transplant. Oct. 2012;27 Suppl 3:iii81-8.
Fox et al., "A multi-marker approach to predict incident CKD and microalbuminuria." J Am Soc Nephrol. Dec. 2010;21(12):2143-9.
Halbesman et al., "Development and validation of a general population renal risk score." Clin J Am Soc Nephrol. Jul. 2011;6(7):1731-8.
Hallan et al., "Combining GFR and albuminuria to classify CKD improves prediction of ESRD." J Am Soc Nephrol. May 2009;20(5):1069-77.
Hellemons et al., "Growth-differentiation factor 15 predicts worsening of albuminuria in patients with type 2 diabetes." Diabetes Care. Nov. 2012;35(11):2340-6.
Hu et al., "Kidney function can improve in patients with hypertensive CKD." J Am Soc Nephrol. Apr. 2012;23(4):706-13.
Keith et al., "Longitudinal follow-up and outcomes among a population with chronic kidney disease in a large managed care organization." Arch Intern Med. Mar. 22, 2004;164(6):659-63.
Lajer et al., "Plasma growth differentiation factor-15 independently predicts all-cause and cardiovascular mortality as well as deterioration of kidney function in type 1 diabetic patients with nephropathy." Diabetes Care. Jul. 2010;33(7):1567-72.
Lapsley et al., "Beta 2-glycoprotein-1 (apolipoprotein H) excretion in chronic renal tubular disorders: comparison with other protein markers of tubular malfunction." J Clin Pathol. Oct. 1991;44(10):812-6.
Lapsley et al., "Beta 2-glycoprotein-1 (apolipoprotein H) excretion and renal tubular malfunction in diabetic patients without clinical proteinuria." J Clin Pathol. May 1993;46(5):465-9.
Li et al., "Longitudinal progression trajectory of GFR among patients with CKD." Am J Kidney Dis. Apr. 2012;59(4):504-12.
Lindeman et al., "Longitudinal studies on the rate of decline in renal function with age." J Am Geriatr Soc. Apr. 1985;33(4):278-85.
Nolan et al., "Suspension array technology: evolution of the flat-array paradigm." Trends Biotechnol. Jan. 2002;20(1):9-12.
Norden et al., "Excretion of beta 2-glycoprotein I (apolipoprotein H) in renal tubular disease." Clin Chem. Jan. 1991;37(1):74-7
O'Seaghdha "Analysis of a urinary biomarker panel for incident kidney disease and clinical outcomes." J Am Soc Nephrol. Nov. 2013;24(11):1880-8.
O'Seaghdha "Elevated galectin-3 precedes the development of CKD." J Am Soc Nephrol. Sep. 2013;24(9):1470-7.
Ranieri et al., "Urinary IL-6/EGF ratio: a useful prognostic marker for the progression of renal damage in IgA nephropathy." Kidney Int. Dec. 1996;50(6):1990-2001.
Richter et al., "Electrochemiluminescence (ECL)." Chem Rev. Jun. 2004;104(6):3003-36.
Sato "Diagnostic and prognostic property of NT-proBNP in patients with renal dysfunction." J Cardiol. Jun. 2013;61(6):446-7.
Spanaus et al., "B-type natriuretic peptide concentrations predict the progression of nondiabetic chronic kidney disease: the Mild-to-Moderate Kidney Disease Study." Clin Chem. Jul. 2007;53(7):1264-72.
Stangou et al., "Detection of multiple cytokines in the urine of patients with focal necrotising glomerulonephritis may predict short and long term outcome of renal function." Cytokine. Jan. 2012;57(1):120-6.
Stangou et al., "Urinary levels of epidermal growth factor, interleukin-6 and monocyte chemoattractant protein-1 may act as predictor markers of renal function outcome in immunoglobulin A nephropathy." Nephrology (Carlton). Sep. 2009;14(6):613-20.
Svensson et al., "NT-pro-BNP is an independent predictor of mortality in patients with end-stage renal disease" Clin Nephrol. Apr. 2009;71(4):380-6.
Swiss Prot Accession No. NP_ 000468; Gene ID NCBI 213, Retrieved Jan. 13, 2017, 8 pages.
Swiss Prot Accession No. NP_000033,Gene ID NCBI 350, Retrieved Jan. 13, 2017, 4 pages.
Swiss Prot Accession No. NP_004855, Gene ID NCBI 9518, Retrieved Jan. 13, 2017, 3 pages.

(56) References Cited

OTHER PUBLICATIONS

Taal "Predicting initiation and progression of chronic kidney disease: Developing renal risk scores." Kidney Int. Nov. 2006;70(10):1694-705.
Taal "Renal risk scores: progress and prospects." Kidney Int. Jun. 2008;73(11):1216-9.
Taal et al., "Defining renal risk." Curr Opin Nephrol Hypertens. Nov. 2007;16(6):554-6.
Torres et al., "The ratio of epidermal growth factor to monocyte chemotactic peptide-1 in the urine predicts renal prognosis in IgA nephropathy." Kidney Int. Feb. 2008;73(3):327-33.
Quiroga et al., "Inflammatory Biomarkers in Chronic Kidney Disease: A Review", Recent Patents on Biomarkers 2012,2, 131-138. Accession No. 605312, Retrieved Nov. 10, 2016, 2 pages.
Wang et al., "N-terminal pro-brain natriuretic peptide: an independent risk predictor of cardiovascular congestion, mortality, and adverse cardiovascular outcomes in chronic peritoneal dialysis patients." J Am Soc Nephrol. Jan. 2007;18(1):321-30.
Xue et al., "Longitudinal study of racial and ethnic differences in developing end-stage renal disease among aged medicare beneficiaries." J Am Soc Nephrol. Apr. 2007;18(4):1299-306.
Yasuda et al., "Plasma B-type natriuretic peptide level predicts kidney prognosis in patients with predialysis chronic kidney disease." Nephrol Dial Transplant. Oct. 2012;27(10):3885-91.
Office action of related CN Application No. 201480072171.3, dated Feb. 28, 2017,16 pages.
Ellam, "Albumin:Creatinine Ratio—A Flawed Measure? The Merits of Estimated Albuminuria Reporting" Nephron Clin Pract 2011;118:c324-c330.
Fischer et al., "Comparison of associations of urine protein-creatinine ratio versus albumin-creatinine ratio with complications of CKD: a cross-sectional analysis." Am J Kidney Dis. Dec. 2013;62(6):1102-8.
Ju et al., "Tissue transcriptome-driven identification of epidermal growth factor as a chronic kidney disease biomarker." Sci Transl Med. Dec. 2, 2015;7(316):316ra193.
Tsau et al.,"Urinary epidermal growth factor excretion in children with chronic renal failure." Am J Nephrol. 1999;19(3):400-4.
Search Report of related EP 14792498.9, dated Jun. 12, 2017, 14 pages.
Jun et al., "Detection of Serum, Urine Epidermal Growth Factor in Chronic NephritisPatients and Significance" Hainan Medical Journal, 2006 vol. 17 (11). p. 66-67.
Jie et al., "The advance in the roles of apolipoprotein H in renal tnbnlar disorders" Joumal of MedicalPostgraduates, 2000, p. 55-57.
Office action of related CN Application No. 201480072171.3, dated Sep. 29, 2017, 18 pages.

* cited by examiner

Figure 1: Information Criteria and Goodness of Fit
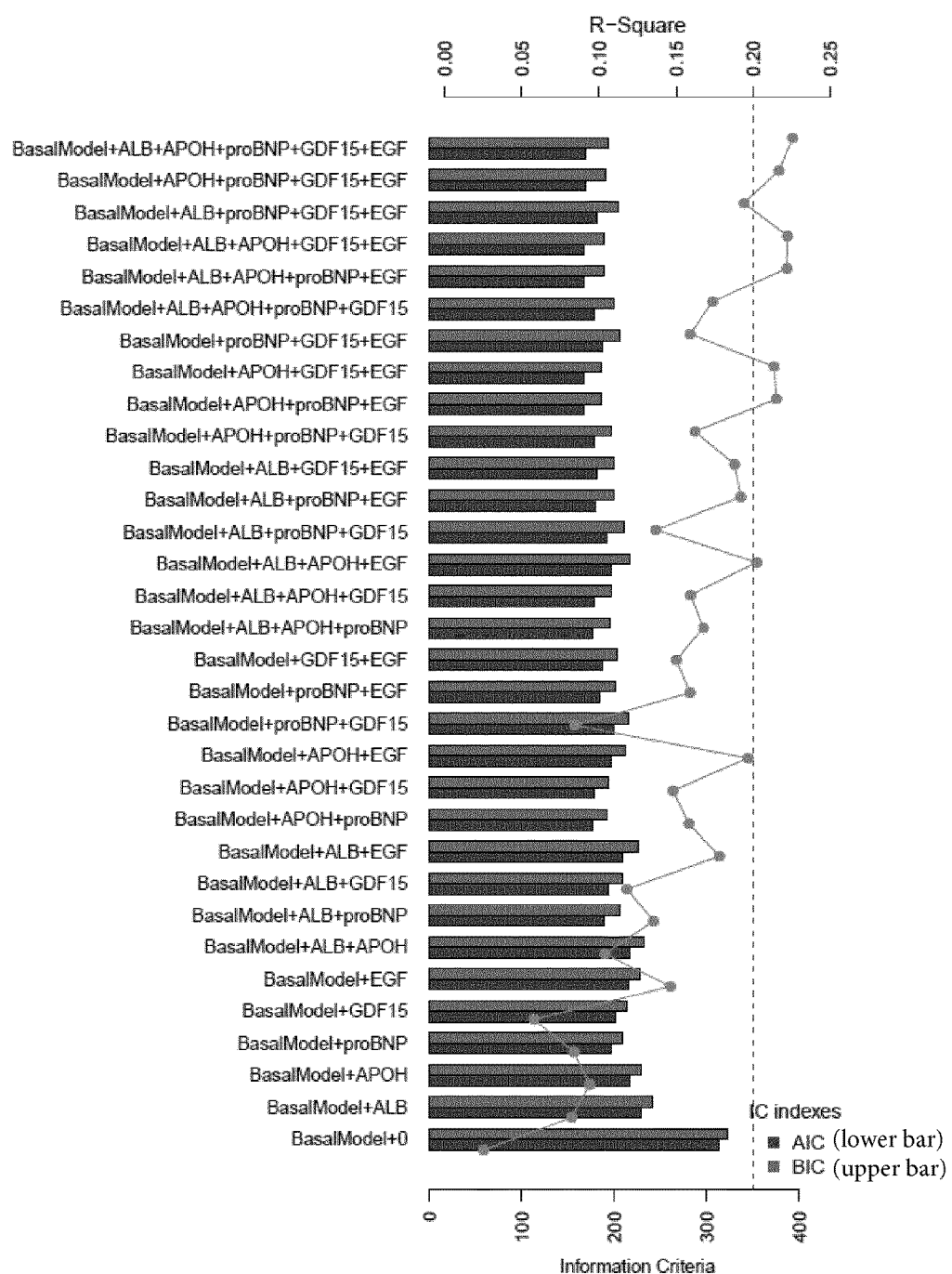

Figure 2: Goodness of Fit All Models

|  | NrParm | Rsq | AIC | BIC | N |
|---|---|---|---|---|---|
| BasalModel+0 | 3 | 0.025 | 312.68 | 322.86 | 220 |
| BasalModel+ALB | 4 | 0.082 | 228.15 | 241.14 | 190 |
| BasalModel+APOH | 4 | 0.094 | 216.55 | 229.43 | 185 |
| BasalModel+proBNP | 4 | 0.084 | 197.09 | 209.54 | 166 |
| BasalModel+GDF15 | 4 | 0.058 | 201.70 | 214.15 | 166 |
| BasalModel+EGF | 4 | 0.146 | 214.39 | 227.38 | 190 |
| BasalModel+ALB+APOH | 5 | 0.104 | 216.52 | 232.62 | 185 |
| BasalModel+ALB+proBNP | 5 | 0.135 | 189.47 | 205.03 | 166 |
| BasalModel+ALB+GDF15 | 5 | 0.118 | 192.74 | 208.30 | 166 |
| BasalModel+ALB+EGF | 5 | 0.178 | 209.17 | 225.41 | 190 |
| BasalModel+APOH+proBNP | 5 | 0.158 | 176.55 | 191.96 | 161 |
| BasalModel+APOH+GDF15 | 5 | 0.148 | 178.52 | 193.92 | 161 |
| BasalModel+APOH+EGF | 5 | 0.197 | 196.31 | 212.41 | 185 |
| BasalModel+proBNP+GDF15 | 5 | 0.084 | 199.00 | 214.56 | 166 |
| BasalModel+proBNP+EGF | 5 | 0.159 | 184.88 | 200.44 | 166 |
| BasalModel+GDF15+EGF | 5 | 0.150 | 186.62 | 202.18 | 166 |
| BasalModel+ALB+APOH+proBNP | 6 | 0.168 | 176.70 | 195.19 | 161 |
| BasalModel+ALB+APOH+GDF15 | 6 | 0.159 | 178.35 | 196.84 | 161 |
| BasalModel+ALB+APOH+EGF | 6 | 0.203 | 196.94 | 216.26 | 185 |
| BasalModel+ALB+proBNP+GDF15 | 6 | 0.137 | 191.20 | 209.88 | 166 |
| BasalModel+ALB+proBNP+EGF | 6 | 0.192 | 180.17 | 198.85 | 166 |
| BasalModel+ALB+GDF15+EGF | 6 | 0.188 | 181.03 | 199.70 | 166 |
| BasalModel+APOH+proBNP+GDF15 | 6 | 0.162 | 177.76 | 196.25 | 161 |
| BasalModel+APOH+proBNP+EGF | 6 | 0.215 | 167.25 | 185.74 | 161 |
| BasalModel+APOH+GDF15+EGF | 6 | 0.214 | 167.55 | 186.04 | 161 |
| BasalModel+proBNP+GDF15+EGF | 6 | 0.159 | 186.85 | 205.52 | 166 |
| BasalModel+ALB+APOH+proBNP+GDF15 | 7 | 0.174 | 177.51 | 199.08 | 161 |
| BasalModel+ALB+APOH+proBNP+EGF | 7 | 0.222 | 167.83 | 189.40 | 161 |
| BasalModel+ALB+APOH+GDF15+EGF | 7 | 0.222 | 167.79 | 189.36 | 161 |
| BasalModel+ALB+proBNP+GDF15+EGF | 7 | 0.194 | 181.77 | 203.55 | 166 |
| BasalModel+APOH+proBNP+GDF15+EGF | 7 | 0.217 | 168.94 | 190.51 | 161 |
| BasalModel+ALB+APOH+proBNP+GDF15+EGF | 8 | 0.226 | 169.07 | 193.72 | 161 |

Figure 3

Table A

| Outcome | Code | Event |
|---|---|---|
| Non Case | 0 | No |
| Transplant | 1 | Yes |
| Dialysis | 2 | Yes |
| Disease Progression | 3 | No |
| Deceased | 4 | Yes |
| *eGFR* < 15 | 5 | No |
| 40% eGFR loss | 6 | Yes |
| 50% eGFR loss | 7 | Yes |

Figure 4

Table B

| | N | Non-Case<br>N = 181 | ESRD at entrance<br>N = 4 | Progr. Decline<br>N = 8 | CKD Hard EP<br>N = 28 |
|---|---|---|---|---|---|
| Age | 221 | 42.0 59.0 67.0 | 53.3 58.0 63.2 | 31.2 48.5 64.5 | 43.0 58.0 67.0 |
| Gender : 2 | 221 | 65% (117) | 25% (1) | 62% (5) | 46% (13) |
| eGFR at BL | 221 | 35.7 48.5 67.2 | 20.3 21.1 21.9 | 40.3 53.5 101.2 | 22.6 31.4 37.5 |
| CKD-stage at BL : 1 - 2 | 221 | 33% (60) | 0% (0) | 38% (3) | 11% (3) |
| 3 | | 51% (93) | 0% (0) | 62% (5) | 39% (11) |
| 4 - 5 | | 15% (28) | 100% (4) | 0% (0) | 50% (14) |
| initial egfr | 221 | 42.8 58.3 80.9 | 25.8 35.4 48.3 | 52.1 70.5 92.3 | 38.3 60.3 77.2 |
| Nr of CKD events | 221 | 0% (0) | 0% (0) | 88% (7) | 100% (28) |
| log(APOH/Cr ng/mg) | 185 | 7.16 8.06 9.27 | 11.06 11.76 12.13 | 8.05 9.14 9.24 | 8.82 12.25 13.68 |
| log(UrineAlb/Cr μg/mg) | 191 | 3.71 7.03 9.46 | 9.97 11.40 11.70 | 7.97 11.36 11.68 | 8.57 10.74 11.16 |
| log(ProBNP pg/ml) | 167 | 5.86 6.88 8.57 | 9.48 10.66 10.77 | 6.62 6.72 6.78 | 7.00 8.89 10.17 |
| log(GDF15plasma pg/ml) | 167 | 10.05 10.58 11.20 | 11.32 11.50 12.27 | 9.61 9.94 10.65 | 10.72 11.18 11.64 |
| log(EGF/Cr ng/mg) | 191 | 2.22 2.66 3.26 | 0.57 1.00 1.00 | 2.40 2.81 3.53 | 0.76 1.30 2.17 | a, b, c represent the lower quartile a, the median b, and the upper quartile c for continuous variables.
N is the number of non-missing values.
Numbers after percents are frequencies.

Figure 5

SEQ ID NO:1   GDF-15   NP_004855

```
  1 MPGQELRTVN GSQMLLVLLV LSWLPHGGAL SLAEASRASF PGPSELHSED
 51 SRFRELRKRY EDLLTRLRAN QSWEDSNTDL VPAPAVRILT PEVRLGSGGH
101 LHLRISRAAL PEGLPEASRL HRALFRLSPT ASRSWDVTRP LRRQLSLARP
151 QAPALHLRLS PPPSQSDQLL AESSSARPQL ELHLRPQAAR GRRRARARNG
201 DHCPLGPGRC CRLHTVRASL EDLGWADWVL SPREVQVTMC IGACPSQFRA
251 ANMHAQIKTS LHRLKPDTVP APCCVPASYN PMVLIQKTDT GVSLQTYDDL
301 LAKDCHCI
```

Figure 6

SEQ ID NO: 2   EGF   NP_001954

```
   1 MLLTLIILLP VVSKFSFVSL SAPQHWSCPE GTLAGNGNST CVGPAPFLIF
  51 SHGNSIFRID TEGTNYEQLV VDAGVSVIMD FHYNEKRIYW VDLERQLLQR
 101 VFLNGSRQER VCNIEKNVSG MAINWINEEV IWSNQQEGII TVTDMKGNNS
 151 HILLSALKYP ANVAVDPVER FIFWSSEVAG SLYRADLDGV GVKALLETSE
 201 KITAVSLDVL DKRLFWIQYN REGSNSLICS CDYDGGSVHI SKHPTQHNLF
 251 AMSLFGDRIF YSTWKMKTIW IANKHTGKDM VRINLHSSFV PLGELKVVHP
 301 LAQPKAEDDT WEPEQKLCKL RKGNCSSTVC GQDLQSHLCM CAEGYALSRD
 351 RKYCEDVNEC AFWNHGCTLG CKNTPGSYYC TCPVGFVLLP DGKRCHQLVS
 401 CPRNVSECSH DCVLTSEGPL CFCPEGSVLE RDGKTCSGCS SPDNGGCSQL
 451 CVPLSPVSWE CDCFPGYDLQ LDEKSCAASG PQPFLLFANS QDIRHMHFDG
 501 TDYGTLLSQQ MGMVYALDHD PVENKIYFAH TALKWIERAN MDGSQRERLI
 551 EEGVDVPEGL AVDWIGRRFY WTDRGKSLIG RSDLNGKRSK IITKENISQP
 601 RGIAVHPMAK RLFWTDTGIN PRIESSSLQG LGRLVIASSD LIWPSGITID
 651 FLTDKLYWCD AKQSVIEMAN LDGSKRRRLT QNDVGHPFAV AVFEDYVWFS
 701 DWAMPSVMRV NKRTGKDRVR LQGSMLKPSS LVVVHPLAKP GADPCLYQNG
 751 GCEHICKKRL GTAWCSCREG FMKASDGKTC LALDGHQLLA GGEVDLKNQV
 801 TPLDILSKTR VSEDNITESQ HMLVAEIMVS DQDDCAPVGC SMYARCISEG
 851 EDATCQCLKG FAGDGKLCSD IDECEMGVPV CPPASSKCIN TEGGYVCRCS
 901 EGYQGDGIHC LDIDECQLGE HSCGENASCT NTEGGYTCMC AGRLSEPGLI
 951 CPDSTPPPHL REDDHHYSVR NSDSECPLSH DGYCLHDGVC MYIEALDKYA
1001 CNCVVGYIGE RCQYRDLKWW ELRHAGHGQQ QKVIVVAVCV VVLVMLLLS
1051 LWGAHYYRTQ KLLSKNPKNP YEESSRDVRS RRPADTEDGM SSCPQPWFVV
1101 IKEHQDLKNG GQPVAGEDGQ AADGSMQPTS WRQEPQLCGM GTEQGCWIPV
1151 SSDKGSCPQV MERSFHMPSY GTQTLEGGVE KPHSLLSANP LWQQRALDPP
1201 HQMELTQ
```

Figure 7

SEQ ID NO: 3    NT-proBNP    NP_002512

```
  1 MDPQTAPSRA LLLLLFLHLA FLGGRSHPLG SPGSASDLET SGLQEQRNHL
 51 QGKLSELQVE QTSLEPLQES PRPTGVWKSR EVATEGIRGH RKMVLYTLRA
101 PRSPKMVQGS GCFGRKMDRI SSSSGLGCKV LRRH
```

Figure 8

SEQ ID NO: 4    ApoH    NP_000033

```
  1 MISPVLILFS SFLCHVAIAG RTCPKPDDLP FSTVVPLKTF YEPGEEITYS
 51 CKPGYVSRGG MRKFICPLTG LWPINTLKCT PRVCPFAGIL ENGAVRYTTF
101 EYPNTISFSC NTGFYLNGAD SAKCTEEGKW SPELPVCAPI ICPPPSIPTF
151 ATLRVYKPSA GNNSLYRDTA VFECLPQHAM FGNDTITCTT HGNWTKLPEC
201 REVKCPFPSR PDNGFVNYPA KPTLYYKDKA TFGCHDGYSL DGPEEIECTK
251 LGNWSAMPSC KASCKVPVKK ATVVYQGERV KIQEKFKNGM LHGDKVSFFC
301 KNKEKKCSYT EDAQCIDGTI EVPKCFKEHS SLAFWKTDAS DVKPC
```

Figure 9

SEQ ID NO: 5   ALBUMIN   NP_000468

```
  1 MKWVTFISLL FLFSSAYSRG VFRRDAHKSE VAHRFKDLGE ENFKALVLIA
 51 FAQYLQQCPF EDHVKLVNEV TEFAKTCVAD ESAENCDKSL HTLFGDKLCT
101 VATLRETYGE MADCCAKQEP ERNECFLQHK DDNPNLPRLV RPEVDVMCTA
151 FHDNEETFLK KYLYEIARRH PYFYAPELLF FAKRYKAAFT ECCQAADKAA
201 CLLPKLDELR DEGKASSAKQ RLKCASLQKF GERAFKAWAV ARLSQRFPKA
251 EFAEVSKLVT DLTKVHTECC HGDLLECADD RADLAKYICE NQDSISSKLK
301 ECCEKPLLEK SHCIAEVEND EMPADLPSLA ADFVESKDVC KNYAEAKDVF
351 LGMFLYEYAR RHPDYSVVLL LRLAKTYETT LEKCCAAADP HECYAKVFDE
401 FKPLVEEPQN LIKQNCELFE QLGEYKFQNA LLVRYTKKVP QVSTPTLVEV
451 SRNLGKVGSK CCKHPEAKRM PCAEDYLSVV LNQLCVLHEK TPVSDRVTKC
501 CTESLVNRRP CFSALEVDET YVPKEFNAET FTFHADICTL SEKERQIKKQ
551 TALVELVKHK PKATKEQLKA VMDDFAAFVE KCCKADDKET CFAEEGKKLV
601 AASQAALGL
```

BIOMARKERS AND METHODS FOR PROGRESSION PREDICTION FOR CHRONIC KIDNEY DISEASE

GOVERNMENT INTERESTS

This invention was made with United States Government support under DK081943 and DK079912 awarded by the National Institutes of Health. The government has certain rights in the invention.

FIELD OF THE INVENTION

The present disclosure relates to the field of diagnostic measures.

BACKGROUND

Epidemiologic studies and clinical registries have reported that chronic kidney disease (CKD) has a discrete increasing prevalence but it is clear that patients with CKD are a heterogeneous group with different diagnosis, diverse disease etiologies, variable prognosis and markedly diverse rate of progressive decline (1, 2) (3). CKD is thought traditionally to follow an unremittingly progressive decline over time, with often an inconstant rate of decline, and even increases in baseline renal function (glomerular filtration rate (GFR)) may also be common(4) (5). Several studies identified risk factors for CKD progression or increased renal function loss, however it is also recognized that only a relatively small percentage of the individuals with CKD eventually progress to end-stage renal disease (ESRD).

Renal disease progression may follow linear and non-linear trajectories with only a minority accelerating swiftly to end-stage kidney disease (6). The prediction of speed or change in disease progression is a challenging disease characteristic to forecast. Nevertheless the ability to identify those individuals at greatest risk of progression that may require intensification of standard therapy from those at low risk to be spared unnecessary intervention may well be the cornerstone strategy to overcome the current limitations in renal clinical development. From a clinical and therapeutic point of view, early detection of fast progressing patients allows a closer monitoring of both adherence and therapeutic efficacy and may guide intensification of standard therapy (7-9). From a drug development perspective, being able to distinguish patients with an increased risk of disease progression from those patients with a lower risk is an essential step for increasing the probability of success and impact of a novel therapeutic approach.

Such a patient stratification protocol would result in increased efficacy with acceptable safety within a desirable development timeframe. Clinical nephrology has suffered so far of the lack of those concrete tools to identify distinct disease dynamic changes that inevitably would help clinical decision making, promote novel therapeutic approaches and bring innovation in the design of Proof-of-Concept (PoC) clinical studies.

Therefore there is a compelling clinical need for novel risk scores, clinical predictors and/or biomarkers to identify individuals with an increased risk of CKD disease progression at the earliest possible stage (11) (12). The need for risk stratification within CKD is particularly great among patients in the general population or primary care because the majority of patients with CKD are first identified in this setting and most are never referred to a nephrologist.

BRIEF SUMMARY OF THE DISCLOSURE

The present disclosure provides biomarkers and methods for the identification of an increased risk of the progression of chronic kidney disease (CKD), or for monitoring chronic kidney disease therapy.

One aspect of the invention provides for a method for identifying a subject suffering from chronic kidney disease as having an increased risk for disease progression, the method comprising a) detecting the amount of one, two, three, four or five biomarkers selected from the group consisting of GDF-15, EGF, NT-proBNP, ApoH, and albumin to creatinine ratio (AUCR) in a sample of the subject; b) comparing the amount of the one, two, three, four or five biomarkers to a reference amount of the one, two, three, four or five biomarkers; and c) identifying the subject as having an increased risk for disease progression if the amount of the one, two, three, four or five biomarkers in the sample is greater than the reference amount of the one, two, three, four or five biomarkers.

In one embodiment, the method comprises a) detecting the amount of GDF-15 in the sample of the subject; b) comparing the amount of GDF-15 to a reference amount of GDF-15; and c) identifying the subject as having an increased risk for disease progression if the amount of the GDF-15 in the sample is greater than the reference amount of GDF-15. In one embodiment, the method comprises a) detecting the amount of EGF in the sample of the subject; b) comparing the amount of EGF to a reference amount of EGF; and c) identifying the subject as having an increased risk for disease progression if the amount of the EGF in the sample is greater than the reference amount of EGF. In one embodiment, the method comprises a) detecting the amount of NT-proBNP in the sample of the subject; b) comparing the amount of NT-proBNP to a reference amount of NT-proBNP; and c) identifying the subject as having an increased risk for disease progression if the amount of the NT-proBNP in the sample is greater than the reference amount of NT-proBNP. In one embodiment, the method comprises a) detecting the amount of ApoH in the sample of the subject; b) comparing the amount of ApoH to a reference amount of ApoH; and c) identifying the subject as having an increased risk for disease progression if the amount of the ApoH in the sample is greater than the reference amount of ApoH, In one embodiment, the method comprises a) detecting the amount of AUCR in the sample of the subject; b) comparing the amount of AUCR to a reference amount of AUCR; and c) identifying the subject as having an increased risk for disease progression if the amount of the AUCR in the sample is greater than the reference amount of AUCR.

Another aspect of the invention provides for a method for identifying a subject suffering from chronic kidney disease as having an increased risk for disease progression, the method comprising a) detecting the amount of ApoH and one or more additional biomarkers selected from the group consisting of GDF-15, EGF, NT-proBNP, and albumin to creatinine ratio (AUCR) in a sample of the subject; b) comparing the amount of ApoH and the one or more additional biomarkers to a reference amount of ApoH and the one or more additional biomarkers; and c) identifying the subject as having an increased risk for disease progression if the amount of ApoH in the sample and the amount of the one or more additional biomarkers is greater than the reference amount of ApoH and the one or more additional biomarkers.

In one embodiment, the one or more additional biomarkers is GDF-15. In one embodiment, the one or more additional biomarkers is EGF. In one embodiment, the one or more additional biomarkers is NT-proBNP. In one embodiment, the one or more additional biomarkers is AUCR. In one embodiment, the one or more additional biomarkers is GDF-15 and EGF. In one embodiment, the one or more additional biomarkers is GDF-15 and NT-proBNP. In one embodiment, the one or more additional biomarkers is GDF-15 and AUCR. In one embodiment, the one or more additional biomarkers is EGF and NT-proBNP. In one embodiment, the one or more additional biomarkers is EGF and AUCR. In one embodiment, he one or more additional biomarkers is NT-proBNP and AUCR. In one embodiment, the one or more additional biomarkers is EGF and AUCR. In one embodiment, the one or more additional biomarkers is GDF-15, NT-proBNP and AUCR. In one embodiment, the one or more additional biomarkers is EGF, NT-proBNP and AUCR. In one embodiment, the one or more additional biomarkers is EGF, GDF-15, and AUCR. In one embodiment, the one or more additional biomarkers is EGF, GDF-15, and NT-proBNP. In one embodiment, the one or more additional biomarkers is EGF, GDF-15, NT-proBNP, and AUCR.

Another aspect of the invention provides for a method for identifying a subject suffering from chronic kidney disease as having an increased risk for disease progression, the method comprising a) detecting the amount of albumin to creatinine ratio (AUCR) and one or more additional biomarkers selected from the group consisting of GDF-15, EGF, NT-proBNP, and ApoH in a sample of the subject; b) comparing the amount of AUCR and the one or more additional biomarkers to a reference amount of AUCR and the one or more additional biomarkers; and c) identifying the subject as having an increased risk for disease progression if the amount of AUCR in the sample and the amount of the one or more additional biomarkers is greater than the reference amount of AUCR and the one or more additional biomarkers.

In one embodiment, the one or more additional biomarkers is GDF-15 In one embodiment, the one or more additional biomarkers is EGF. In one embodiment, the one or more additional biomarkers is NT-proBNP. In one embodiment, the one or more additional biomarkers is ApoH. In one embodiment, the one or more additional biomarkers is GDF-15 and EGF. In one embodiment, the one or more additional biomarkers is GDF-15 and NT-proBNP. In one embodiment, the one or more additional biomarkers is GDF-15 and ApoH. In one embodiment, the one or more additional biomarkers is EGF and NT-proBNP. In one embodiment, the one or more additional biomarkers is EGF and ApoH. In one embodiment, the the one or more additional biomarkers is NT-proBNP and ApoH. In one embodiment, the he one or more additional biomarkers is EGF and ApoH. In one embodiment, the one or more additional biomarkers is GDF-15, NT-proBNP and ApoH. In one embodiment, the one or more additional biomarkers is EGF, NT-proBNP and ApoH. In one embodiment, the one or more additional biomarkers is EGF, GDF-15, and ApoH. In one embodiment, the one or more additional biomarkers is EGF, GDF-15, and NT-proBNP. In one embodiment, the one or more additional biomarkers is EGF, GDF-15, NT-proBNP, and ApoH.

Another aspect of the invention provides for a method for identifying a subject suffering from chronic kidney disease as having an increased risk for disease progression, the method comprising detecting the amount of NT-proBNP and one or more additional biomarkers selected from the group consisting of GDF-15, EGF, albumin to creatinine ratio (AUCR), and ApoH in a sample of the subject; b) comparing the amount of NT-proBNP and the one or more additional biomarkers to a reference amount of NT-proBNP and the one or more additional biomarkers; and c) identifying the subject as having an increased risk for disease progression if the amount of NT-proBNP in the sample and the amount of the one or more additional biomarkers is greater than the reference amount of NT-proBNP and the one or more additional biomarkers.

In one embodiment, the one or more additional biomarkers is GDF-15. In one embodiment, the one or more additional biomarkers is EGF. In one embodiment, the he one or more additional biomarkers is AUCR. In one embodiment, the one or more additional biomarkers is ApoH. In one embodiment, the one or more additional biomarkers is GDF-15 and EGF. In one embodiment, the one or more additional biomarkers is GDF-15 and AUCR. In one embodiment, the one or more additional biomarkers is GDF-15 and ApoH. In one embodiment, the one or more additional biomarkers is EGF and AUCR. In one embodiment, the one or more additional biomarkers is EGF and ApoH. In one embodiment, the one or more additional biomarkers is AUCR and ApoH. In one embodiment, the one or more additional biomarkers is EGF and ApoH. In one embodiment, the one or more additional biomarkers is GDF-15, AUCR and ApoH. In one embodiment, the one or more additional biomarkers is EGF, AUCR, and ApoH. In one embodiment, the one or more additional biomarkers is EGF, GDF-15, and ApoH. In one embodiment, the one or more additional biomarkers is EGF, GDF-15, and AUCR In one embodiment, the one or more additional biomarkers is EGF, GDF-15, AUCR, and ApoH.

Another aspect of the invention provides for a method for identifying a subject suffering from chronic kidney disease as having an increased risk for disease progression, the method comprising a) detecting the amount of GDF-15 and one or more additional biomarkers selected from the group consisting of NT-proBNP, EGF, albumin to creatinine ratio (AUCR), and ApoH in a sample of the subject; b) comparing the amount of GDF-15 and the one or more additional biomarkers to a reference amount of GDF-15 and the one or more additional biomarkers; and c) identifying the subject as having an increased risk for disease progression if the amount of GDF-15 in the sample and the amount of the one or more additional biomarkers is greater than the reference amount of GDF-15 and the one or more additional biomarkers.

In one embodiment, the one or more additional biomarkers is NT-proBNP. In one embodiment, the one or more additional biomarkers is EGF. In one embodiment, the one or more additional biomarkers is AUCR. In one embodiment, the one or more additional biomarkers is ApoH. In one embodiment, the one or more additional biomarkers is NT-proBNP and EGF. In one embodiment, the one or more additional biomarkers is NT-proBNP and AUCR. In one embodiment, the one or more additional biomarkers is NT-proBNP and ApoH. In one embodiment, the one or more additional biomarkers is EGF and AUCR. In one embodiment, the one or more additional biomarkers is EGF and ApoH. In one embodiment, the one or more additional biomarkers is AUCR and ApoH. In one embodiment, the one or more additional biomarkers is EGF and ApoH. In one embodiment, the one or more additional biomarkers is NT-proBNP, AUCR and ApoH. In one embodiment, the one or more additional biomarkers is EGF, AUCR, and ApoH In one embodiment, the one or more additional biomarkers is EGF, NT-proBNP, and ApoH. In one embodiment, the one or more additional biomarkers is EGF, NT-proBNP, and AUCR. In one embodiment, the one or more additional biomarkers is EGF, NT-proBNP, AUCR, and ApoH.

Another aspect of the invention provides for a method for identifying a subject suffering from chronic kidney disease as having an increased risk for disease progression, the method comprising a) detecting the amount of EGF and one or more additional biomarkers selected from the group consisting of NT-proBNP, GDF-15, albumin to creatinine ratio (AUCR), and ApoH in a sample of the subject; b) comparing the amount of EGF and the one or more additional biomarkers to a reference amount of EGF and the one or more additional biomarkers; and c) identifying the subject as having an increased risk for disease progression if the amount of EGF in the sample and the amount of the one or more additional biomarkers is greater than the reference amount of EGF and the one or more additional biomarkers.

In one embodiment, the one or more additional biomarkers is NT-proBNP. In one embodiment, the one or more additional biomarkers is GDF-15. In one embodiment, the one or more additional biomarkers is AUCR. In one embodiment, the one or more additional biomarkers is ApoH. In one embodiment, the one or more additional biomarkers is NT-proBNP and GDF-15. In one embodiment, the one or more additional biomarkers is NT-proBNP and AUCR. In one embodiment, the one or more additional biomarkers is NT-proBNP and ApoH. In one embodiment, the one or more additional biomarkers is GDF-15 and AUCR. In one embodiment, the one or more additional biomarkers is GDF-15 and ApoH. In one embodiment, the one or more additional biomarkers is AUCR and ApoH. In one embodiment, the one or more additional biomarkers is GDF-15 and ApoH. In one embodiment, the one or more additional biomarkers is NT-proBNP, AUCR and ApoH. In one embodiment, the one or more additional biomarkers is GDF-15, AUCR, and ApoH. In one embodiment, the one or more additional biomarkers is GDF-15, NT-proBNP, and ApoH. In one embodiment, the one or more additional biomarkers is GDF-15, NT-proBNP, and AUCR. In one embodiment, the one or more additional biomarkers is GDF-15, NT-proBNP, AUCR, and ApoH.

In certain embodiments of the above aspects, the detecting comprises contacting, in vitro, the sample with a combination of detection agents, each agent having specific binding affinity for one of the biomarkers.

In certain embodiments, the agent is antibody or fragment thereof.

In certain embodiments of the above aspects, the sample is a serum or urine sample.

In certain embodiments of the above aspects, the subject is identified as having an increased risk of disease progression when the amount of the biomarkers in the sample is greater than the median of the reference amount. In certain embodiments of the above aspects, the subject is identified as having an increased risk of disease progression when the amount of the biomarkers in the sample is in the fourth quartile range of the reference amount.

In certain embodiments, the method further comprises the step of recommending a therapy to treat the chronic kidney disease, if the subject is identified as having an increased risk for disease progression.

In certain embodiments, the method further comprises the step of administering to the subject a pharmaceutical agent to treat the chronic kidney disease, if the subject is identified as having an increased risk for disease progression. The therapy can comprises, for example, an investigational new drug therapy.

Another aspect of the invention provides for a device adapted for carrying out the method of any of the proceeding claims comprising: a) an analysing unit comprising a combination of detection agents which specifically bind to the biomarkers, the analysing unit adapted for contacting, in vitro, the sample from the subject with the detection agent; b) an evaluation unit including a computing device having a database and a computer-implemented algorithm on the database, the computer-implemented algorithm when executed by the computing device determines an amount of the biomarker in the sample from the subject and compares the determined amount of the biomarker with a biomarker reference amount and provides a diagnosis of at increased risk for disease progression if the amount of the biomarker determined in the step of determining is greater than the biomarker reference amount. In one embodiment, the database further includes the biomarker reference amount.

Another aspect of the invention provides for a kit adapted for carrying out the method of any of the proceeding claims, comprising a detection agent for the biomarkers and instructions for carrying out the method. In one embodiment, the kit further comprises a combination of detection agents for the biomarkers.

BRIEF DESCRIPTION OF THE FIGURES

FIGS. 1-2 shows the results of the statistical analysis of each biomarker and combinations thereof in relation to time to CKD event.

FIG. 3 shows Table A which provides a listing of CKD events evaluated from the C-PROBE study cohort of patients.

FIG. 4 shows Table B which provides a listing of patient characteristics and summary statistics evaluated from the C-PROBE study cohort of patients.

FIG. 5 shows exemplary amino acid sequences of GDF-15 (SEQ ID NO: 1).

FIG. 6 shows an exemplary amino acid sequence of EGF (SEQ ID NO: 2).

FIG. 7 shows an exemplary amino acid sequence of NT-proBNP (SEQ ID NO: 3).

FIG. 8 shows an exemplary amino acid sequence of ApoH (SEQ ID NO: 4).

FIG. 9 shows an exemplary amino acid sequence of Albumin (SEQ ID NO: 5)

DETAILED DESCRIPTION OF THE DISCLOSURE

Definitions

The term "chronic kidney disease" (CKD) refers to a condition defined as abnormalities of kidney structure or function, present for months, with implications for health which can occur abruptly, and either resolve or become chronic (Clinical Practice Guideline for the Evaluation and Management of Chronic Kidney Disease Guidelines (KDIGO 2012). CKD is a general term for heterogeneous disorders affecting kidney structure and function with variable clinical presentation, in part related to cause, severity and the rate of progression (Kidney International Supplements (2013) 3, vii).

Definition and identification of CKD is defined with the following criteria:
  1. For individuals at higher risk of progression, and/or where measurement will impact therapeutic decisions
  2. Recognize that small fluctuations in GFR are common and are not necessarily indicative of progression.

3. Define CKD progression based on one of more of the following (Not Graded):
   a. Decline in GFR category (Z90 [G1], 60-89 [G2], 45-59 [G3a], 30-44 [G3b], 15-29 [G4], o15 [G5] ml/min/1.73 m2). A certain drop in eGFR is defined as a drop in GFR category accompanied by a 50% or greater drop in eGFR from baseline_or End-Stage Renal Disease (ESRD, eGFR<15 ml/min/1 73 m2, Renal Replacement Therapy or death or composite of the above parameters.
   b. Rapid progression is defined as a sustained decline in eGFR of more than −3.3% per year.
   c. The confidence in assessing progression is increased with increasing number of serum creatinine measurements and duration of follow-up This damage can cause wastes to build up in the body and lead to other health problems, including cardiovascular disease (CVD), anemia, and bone disease. CKD is usually an irreversible and progressive disease and can lead to kidney failure, also called End Stage Renal Disease (ESRD), over time if it is not treated The term "GDF-15" refers to Growth-Differentiation Factor-15, also known as MIC-1 (Macrophage inhibitory cytokine 1), a member of the transforming growth factor beta (TGF-beta.) cytokine superfamily, exemplified by SEQ ID NO:1, shown in FIG. 5 (Swiss Prot Accession Number NP_004855, Gene ID NCBI 9518); WO99/06445, WO00/70051, WO2005/113585. "GDF-15" encompasses the protein having the amino acid sequence of SEQ ID NO: 1 as well as GDF-15 variants, homologues and isoforms thereof. Such variants, homologues and isoforms have at least the same essential biological and immunological properties as the specific GDF-15. For example, they share the same essential biological and immunological properties if they are detectable by the same specific assays referred to in this specification, e.g., by ELISA assays using polyclonal or monoclonal antibodies specifically recognizing the GDF-15 polypeptides. Exemplary assays are described in the accompanying Examples. Variants referred to above may be allelic variants or any other species specific homologs, paralogs, or orthologs. Moreover, the variants referred to herein include fragments of the specific GDF-15 polypeptides or the aforementioned types of variants as long as these fragments have the essential immunological and biological properties as referred to above. Such fragments may be, e.g., degradation products of the GDF-15 polypeptides. Further included are variants which differ due to posttranslational modifications such as phosphorylation or myristylation.

The term "EGF" refers the peptide growth factor, exemplified by SEQ ID NO: 2, shown in FIG. 6 (Swiss Prot Accession Number NP_001954, Gene ID NCBI 1950). "EGF" encompasses the protein having the amino acid sequence of SEQ ID NO: 2 as well as variants, homologues and isoforms thereof. Such variants, homologues and isoforms have at least the same essential biological and immunological properties as the specific EGF. For example, they share the same essential biological and immunological properties if they are detectable by the same specific assays referred to in this specification, e.g., by ELISA assays using polyclonal or monoclonal antibodies specifically recognizing the EGF polypeptides. Exemplary assays are described in the accompanying Examples. Variants referred to above may be allelic variants or any other species specific homologs, paralogs, or orthologs. Moreover, the variants referred to herein include fragments of the specific EGF polypeptides or the aforementioned types of variants as long as these fragments have the essential immunological and biological properties as referred to above. Such fragments may be, e.g., degradation products of the EGF polypeptides. Further included are variants which differ due to posttranslational modifications such as phosphorylation or myristylation.

The term "NT-proBNP" refers to Amino-terminal proBNP, exemplified by SEQ ID NO: 3, shown in FIG. 7 (Swiss Prot Accession Number NP_002512.1, Gene ID NCBI 4879), WO 02/089657, WO 02/083913, EP 0 648 228. "NT-proBNP" encompasses the protein having the amino acid sequence of SEQ ID NO: 3 as well as variants, homologues and isoforms thereof. Such variants, homologues and isoforms have at least the same essential biological and immunological properties as the specific NT-proBNP. For example, they share the same essential biological and immunological properties if they are detectable by the same specific assays referred to in this specification, e.g., by ELISA assays using polyclonal or monoclonal antibodies specifically recognizing the NT-proBNP polypeptides. Exemplary assays are described in the accompanying Examples. Variants referred to above may be allelic variants or any other species specific homologs, paralogs, or orthologs. Moreover, the variants referred to herein include fragments of the specific NT-proBNP polypeptides or the aforementioned types of variants as long as these fragments have the essential immunological and biological properties as referred to above. Such fragments may be, e.g., degradation products of the NT-proBNP polypeptides. Further included are variants which differ due to posttranslational modifications such as phosphorylation or myristylation.

The term "ApoH" refers to Apolipoprotein H, exemplified by SEQ ID NO: 4, shown in FIG. 8 (Swiss Prot Accession Number NP_000033,Gene ID NCBI 350). "ApoH" encompasses the protein having the amino acid sequence of SEQ ID NO: 4 as well as variants, homologues and isoforms thereof. Such variants, homologues and isoforms have at least the same essential biological and immunological properties as the specific ApoH. For example, they share the same essential biological and immunological properties if they are detectable by the same specific assays referred to in this specification, e.g., by ELISA assays using polyclonal or monoclonal antibodies specifically recognizing the ApoH polypeptides. Exemplary assays are described in the accompanying Examples. Variants referred to above may be allelic variants or any other species specific homologs, paralogs, or orthologs. Moreover, the variants referred to herein include fragments of the specific ApoH polypeptides or the aforementioned types of variants as long as these fragments have the essential immunological and biological properties as referred to above. Such fragments may be, e.g., degradation products of the ApoH polypeptides. Further included are variants which differ due to posttranslational modifications such as phosphorylation or myristylation.

The term "AUCR" refers to the ratio of albumin to creatinine in a sample. This ratio is a known measure of kidney function (KDIGO 2012), albumin SEQ ID NO: 5, shown in FIG. 9 (Swiss Prot Accession Number NP_000468; Gene ID NCBI 213). "Albumin" encompasses the protein having the amino acid sequence of SEQ ID NO: 5 as well as variants, homologues and isoforms thereof. Such variants, homologues and isoforms have at least the same essential biological and immunological properties as the specific Albumin For example, they share the same essential biological and immunological properties if they are detectable by the same specific assays referred to in this specification, e.g., by ELISA assays using polyclonal or monoclonal antibodies specifically recognizing the albumin polypeptides. Exemplary assays are described in the accompanying Examples. Variants referred to above may be allelic variants or any other species specific homologs, paralogs, or orthologs. Moreover, the variants referred to herein include fragments of the specific albumin polypeptides or the aforementioned types of variants as long as these fragments have the essential immunological and biological properties as referred to above. Such fragments may be, e.g., degradation products of the albumin polypeptides. Further included are variants which differ due to posttranslational modifications such as phosphorylation or myristylation.

The term "increased risk for disease progression" as used herein means that the subject to be analyzed by the method of the present disclosure is allocated either into the group of subjects of a population having a normal (i.e., non-elevated) risk for disease progression or into a group of subjects having a significantly elevated risk. An increased risk as referred to in accordance with the present disclosure means that the risk of disease progression within a predetermined predictive window is elevated significantly for a subject with respect to the average risk for disease progression in a population of subjects.

The term "diagnosing" or "identifying" or "assessing" as used herein means predicting whether the risk for disease progression is increased in a subject suffering from chronic kidney disease, or not. As will be understood by those skilled in the art, such a prediction is usually not intended to be correct for 100% of the subjects to be diagnosed. The term, however, requires that the prediction to be at increased risk for disease progression, or not, is correct for a statistically significant portion of the subjects (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Example confidence intervals are at least 90%, at least 95%, at least 97%, at least 98% or at least 99%. The p-values include 0.1, 0.05, 0.01, 0.005, or 0.0001.

The phrase "providing a diagnosis/assessment" as used herein refers to using the information or data generated relating to the level or presence of the biomarker(s) in a sample of a patient to diagnose/assess the risk of CKD disease progression in the patient. The information or data may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of the biomarker(s) to a reference level. In some embodiments, the information or data includes an indication that the biomarker(s) is present or absent in the sample. In some embodiments, the information or data includes an indication that the patient is diagnosed/assessed with an increased risk of CKD disease progression.

The term "subject" as used herein relates to animals, such as mammals (for example, humans). The subject according to the present disclosure shall suffer from chronic kidney disease as described elsewhere herein.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, bronchial lavage or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation.

The term "detecting" the amount of a biomarker peptide or polypeptide as used herein refers to measuring the amount or concentration, semi-quantitatively or quantitatively for example. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

The term "comparing" as used herein refers to comparing the level of the biomarker in the sample from the individual or patient with the reference level of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. Thus, the comparison may be carried out by a computing device (e.g., of a system disclosed herein). The value of the measured or detected level of the biomarker in the sample from the individual or patient and the reference level can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the determined amount may be compared to values corresponding to suitable references which are stored in a database by a computer program. The computer program may further evaluate the result of the comparison, i.e. automatically provide the desired assessment in a suitable output format. For a computer assisted comparison, the value of the determined amount may be compared to values corresponding to suitable references which are stored in a database by a computer program. The computer program may further evaluate the result of the comparison, i.e. automatically provides the desired assessment in a suitable output format.

Accordingly, the term "reference amount" as used herein refers to an amount which allows assessing whether a subject suffering from CKD has an increased risk disease progression. The reference may e.g. be derived from a pool of subjects suffering from CKD or a pool of subjects from the general population. Moreover, the reference amount may define a threshold amount or range, whereby dependent on the type of reference a change in the determined amount with respect to the threshold is either indicative for an increased risk for disease progression or a normal risk. Alternatively, an essentially identical amount may be either indicative for an increased risk for disease progression or a normal risk as well, if a suitable reference amount is used. The reference amount applicable for an individual subject may vary depending on various physiological parameters such as age, gender, or subpopulation, as well as on the means used for the determination of the polypeptide or peptide referred to herein. A suitable reference amount may be determined from a reference sample to be analyzed together, i.e. simultaneously or subsequently, with the test sample.

The term "monitoring" as referred to above relates to keeping track of the status of the disease, i.e. chronic kidney disease. Monitoring includes comparing the status of the disease as reflected by the amount of the biomarker in a first sample taken at a first time point to the status of the disease reflected by the amount of the biomarker in a second sample taken at a second time point. The status of the disease may become worse and, thus, there will be progression of the disease, if the amount of the biomarker increases whereas there is amelioration and, thus, improvement of the status of the disease if the biomarker decreases. If no change is observed, i.e. an essentially identical amount is determined in the first and the second sample, the status of the disease is unchanged and the disease, thus, is stagnating. An essentially identical amount is determined if no statistically significant change in the amount is determined between the first and the second sample. Whether the amounts are essentially identical can be determined by the skilled artisan without further ado. A change, i.e. increase or decrease is statistically significant if the amounts differ by at least about 5%, at least about 10%, at least about 15%, at least about 20%, at least about 25% or at least about 50%. Again, it is to be understood that the aforementioned method allows monitoring in a statistically significant portion of subjects to investigated but not necessarily in all analyzed subjects.

The term "binding agent" refers to a molecule that comprises a binding moiety which specifically binds the corresponding target biomarker molecule. Examples of "binding agent" are a nucleic acid probe, nucleic acid primer, DNA molecule, RNA molecule, aptamer, antibody, antibody fragment, peptide, peptide nucleic acid (PNA) or chemical compound.

The term "aptamer" refers to oligonucleotides, including RNA, DNA and RNA/DNA molecules, or peptide molecules, which exhibit the desired biological activity, in particular, binding to the corresponding target molecule.

The term "probe" or "nucleic acid probe" refers to a nucleic acid molecule that is capable of hybridizing with a target nucleic acid molecule (e.g., genomic target nucleic acid molecule) and, when hybridized to the target, is capable of being detected either directly or indirectly. Thus probes permit the detection, and in some examples quantification, of a target nucleic acid molecule. In particular examples, a probe includes a plurality of nucleic acid molecules, which include binding regions derived from the target nucleic acid molecule and are thus capable of specifically hybridizing to at least a portion of the target nucleic acid molecule. A probe can be referred to as a "labeled nucleic acid probe," indicating that the probe is coupled directly or indirectly to a detectable moiety or "label," which renders the probe detectable.

The term "primer" or "nucleic acid primer" refers to a short single stranded polynucleotide, generally with a free 3'-OH group, which binds to a target molecule potentially present in a sample of interest by hybridizing with a target sequence, and thereafter promotes polymerization of a polynucleotide complementary to the target.

The term "specific binding" or "specifically bind" refers to a binding reaction wherein binding pair molecules exhibit a binding to each other under conditions where they do not significantly bind to other molecules.

The term "specific binding" or "specifically binds", when referring to a protein or peptide as a binding agent, refers to a binding reaction wherein a binding agent binds to the corresponding target molecule with an affinity of at least 10-7 M. The term "specific binding" or "specifically binds" preferably refers to an affinity of at least 10-8 M or even more preferred of at least 10-9 M for its target molecule. The term "specific" or "specifically" is used to indicate that other molecules present in the sample do not significantly bind to the binding agent specific for the target molecule. Preferably, the level of binding to a molecule other than the target molecule results in a binding affinity which is only 10% or less, more preferably only 5% or less of the affinity to the target molecule.

The term "specific binding" or "specifically binds", when referring to a nucleic acid as a binding agent, refers to a hybridization reaction wherein a binding agent or a probe contains a hybridizing region exactly or substantially complementary to the target sequence of interest. A hybridization assay carried out using the binding agent or probe under sufficiently stringent hybridization conditions enables the selective detection of the specific target sequence. The hybridizing region is preferably from about 10 to about 35 nucleotides in length, more preferably from about 15 to about 35 nucleotides in length. The use of modified bases or base analogues which affect the hybridization stability, which are well known in the art, may enable the use of shorter or longer probes with comparable stability. A binding agent or a probe can either consist entirely of the hybridizing region or can contain additional features which allow for the detection or immobilization of the probe, but which do not significantly alter the hybridization characteristics of the hybridizing region.

The term "specific binding" or "specifically binds", when referring to a nucleic acid aptamer as a binding agent, refers to a binding reaction wherein a nucleic acid aptamer binds to the corresponding target molecule with an affinity in the low nM to pM range.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "amount" as used herein encompasses the absolute amount of a polypeptide or peptide, the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "device" as used herein relates to a system comprising the aforementioned units operatively linked to each other as to allow the diagnosis or monitoring according to the methods of the disclosure. Example detection agents which can be used for the analyzing unit are disclosed elsewhere herein. The analyzing unit may comprise said detection agents in immobilized form on a solid support which is to be contacted to the sample comprising the biomarkers the amount of which is to be determined. Moreover, the analyzing unit can also comprise a detector which determines the amount of detection agent which is specifically bound to the biomarker(s). The determined amount can be transmitted to the evaluation unit. Said evaluation unit comprises a data processing element, such as a computer, with an implemented algorithm for carrying out a comparison between the determined amount and a suitable reference.

The term "kit" as used herein refers to a collection of the aforementioned components which may be provided separately or within a single container. The container also comprises instructions for carrying out the method of the present disclosure. These instructions may be in the form of a manual or may be provided by a computer program code which is capable of carrying out the comparisons referred to in the methods of the present disclosure and to establish a diagnosis accordingly when implemented on a computer or a data processing device. The computer program code may be provided on a data storage medium or device such as an optical storage medium (e.g., a Compact Disc) or directly on a computer or data processing device.

Illustrative Embodiments

Clinical risk prediction models incorporate multiple variables to prognosticate the risk of adverse events for an individual patient and should be able to predict renal endpoints and well as all-cause mortality and cardiovascular disease in CKD patients. Proteinuria, hypertension, diabetes, race, and ethnicity are strong risk factors for progression from CKD to ESRD (13). The biomarker approach described herein reflects the various pathways involved in the pathogenesis of CKD and provides a surrogate representation of disease course of progression and prediction of long term outcomes. The use and implementation of this approach can be used to identify segments of the CKD population that would benefit most from a novel treatment. Clinical use of the biomarker and methods described herein is useful in identifying which patients may need a more aggressive treatment and avoid additional therapeutic options or dose escalation in patients with a lowest risk of progression. Embodiments of the instant disclosure also encompass diagnostic devices and kits for carrying out the aforementioned methods.

One aspect of the present disclosure relates to methods for diagnosing whether a subject suffering from chronic kidney disease (CKD) is at increased risk for disease progression. In one embodiment, the method comprises detecting the amount of one or more of the biomarkers GDF-15, EGF, NT-proBNP, ApoH, and albumin to creatinine ratio (AUCR) in a sample of the subject and comparing the amount to a reference. The subject is identified as having an increased risk of disease progression if the amount of one, two, three, four or all five biomarkers in the sample is greater than the reference amount of the one, two, three, four or five biomarkers.

Another aspect of the present disclosure relates to methods for monitoring whether a subject suffering from chronic kidney disease (CKD) is at increased risk for disease progression during the course of treatment for CKD. In one embodiment, the method comprises detecting the amount of one or more of the biomarkers GDF-15, EGF, NT-proBNP, ApoH, and albumin to creatinine ratio (AUCR) in a sample of the subject and comparing the amount to a reference. The subject is identified as having an increased risk of disease progression if the amount of one, two, three, four or all five biomarkers in the sample is greater than the reference amount of the one, two, three, four or five biomarkers. In one embodiment, the reference is from a sample of subjects suffering from CKD. In another embodiment, the reference is sample taken from the subject prior to beginning treatment for CKD or a sample taken from the subject at a timepoint during the treatment process. The treatment may be modified based on the results of this method. For example, the treatment may be continued if the subject exhibits a decrease in the amount of biomarker(s) as compared to the reference. Conversely, the treatment may be substituted for an alternative treatment if the subject exhibits an increase in the amount of biomarker(s) as compared to the reference.

Another aspect of the invention relates to a device adapted for carrying out the methods provided above and herein is provided. Exemplary embodiments of the device comprise a) an analysing unit comprising a detection agent which specifically binds to a biomarker of the invention, said analysing unit adapted for contacting, in vitro, a portion of a sample from the subject with the detection agent; b) an evaluation unit including a computing device having a database and a computer-implemented algorithm on the database, the computer-implemented algorithm when executed by the computing device determines an amount of the biomarker in the sample from the subject and compares the determined amount of the biomarker with a biomarker reference amount and provides a diagnosis of at increased risk for disease progression if the amount of the biomarker determined in said step of determining is greater than the biomarker reference amount. According to some embodiments, the database further includes the biomarker reference amount.

Another aspect of the invention provides for a kit adapted for carrying out the above disclosed methods of the present disclosure comprising a detection agent for the biomarker(s) as well as instructions for carrying out the method. In one embodiment, the kit is for diagnosing whether a subject suffering from chronic kidney disease (CKD) is at increased risk for disease progression.

In any of the above aspects and methods, the biomarker or biomarkers are selected from among GDF-15, EGF, NT-proBNP, ApoH, and albumin to creatinine ratio (AUCR).

In one embodiment of the aspects and methods, one, two, three, four or five biomarkers are selected from the group consisting of GDF-15, EGF, NT-proBNP, ApoH, and AUCR. In certain embodiments, the following combinations are specifically contemplated:
AUCR+ApoH
AUCR+NT-proBNP
AUCR+GDF-15
AUCR+EGF
ApoH+NT-proBNP
ApoH+GDF-15
ApoH+EGF
NT-proBNP+GDF-15
NT-proBNP+EGF
GDF-15+EGF
AUCR+ApoH+NT-proBNP
AUCR+ApoH+GDF
AUCR+ApoH+EGF
AUCR+NT-proBNP+GDF-15
AUCR+NT-proBNP+EGF
AUCR+GDF-15+EGF
ApoH+NT-proBNP+GDF-15
ApoH+NT-proBNP+EGF
ApoH+GDF-15
NT-proBNP+GDF-15+EGF
AUCR+ApoH+NT-proBNP+GDF-15
AUCR+ApoH+NT-proBNP+EGF
AUCR+ApoH+GDF-15+EGF
AUCR+NT-proBNP+GDF-15+EGF
ApoH+NT-proBNP+GDF-15+EGF
AUCR+ApoH+NT-proBNP+GDF-15+EGF In one embodiment, the amounts of at least one, at least two, at least three, at least four, or all five of the biomarkers determined in the test sample are increased as compared to the reference amounts for the biomarkers is indicative for a subject who has an increased risk of disease progression.

In one embodiment, the amounts of all biomarkers markers determined in the test sample are increased as compared to the reference amounts for the biomarkers is indicative for a subject who has an increased risk of disease progression.

In one embodiment, the subject is identified as having an increased risk of disease progression if the amount of at least one, at least two, at least three, at least four, or all five of the biomarkers determined in the test sample is greater than the reference amount. In one embodiment, the reference amount is the median amount derived from a cohort of patients suffering from CKD.

In one embodiment, the subject is identified as having an increased risk of disease progression if the amount of at least one, at least two, at least three, at least four, or all five of the biomarkers determined in the test sample is at, or greater, than the second, third, or fourth quartile based on the quartiles derived from a cohort of patients suffering from CKD. In one embodiment, the reference amount is in the fourth quartile based on the quartiles derived from a cohort of patients suffering from CKD.

Methods of Detecting the Biomarkers

Biomarkers, including proteins or nucleic acids, can be detected using methods generally known in the art. Methods of detection generally encompass methods to quantify the level of a biomarker in the sample (quantitative method) or that determine whether or not a biomarker is present in the sample (qualitative method). It is generally known to the skilled artisan which of the following methods are suitable for qualitative and/or for quantitative detection of a biomarker. Samples can be conveniently assayed for, e.g., proteins using Westerns and immunoassays, like ELISAs, RIAs, fluorescence-based immunoassays, as well as mRNAs or DNAs from a genetic biomarker of interest using Northern, dot-blot, polymerase chain reaction (PCR) analysis, array hybridization, RNase protection assay, or using DNA SNP chip microarrays, which are commercially available, including DNA microarray snapshots. Further suitable methods to detect biomarker include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins a wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used immunoassays.

Methods for measuring electrochemiluminescent phenomena are well-known. Such methods make use of the ability of special metal complexes to achieve, by means of oxidation, an excited state from which they decay to ground state, emitting electrochemiluminescence. For review see Richter, M. M., Chem. Rev. 104 (2004) 3003-3036.

Biomarkers can also be detected by generally known methods including magnetic resonance spectroscopy (NMR spectroscopy), Gas chromatography-mass spectrometry (GC-MS), Liquid chromatography-mass spectrometry (LC-MS), High and ultra-HPLC HPLC such as reverse phase HPLC, for example, ion-pairing HPLC with dual UV-wavelength detection, capillary electrophoresis with laser-induce fluorescence detection, anion exchange chromatography and fluorescent detection, thin layer chromatography.

In accordance with the present disclosure, detecting the amount of a biomarker peptide or polypeptide can be achieved by all known means for determining the amount of a peptide in a sample. Examples of such means include immunoassay devices and methods which may utilize labeled molecules in various sandwich, competition, or other assay formats. These assays will develop a signal which is indicative for the presence or absence of the peptide or polypeptide. Moreover, the signal strength can be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. These methods may comprise biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

According to the instant disclosure, determining the amount of a biomarker peptide or polypeptide may comprise the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample may be added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide. Also, detecting the amount of a biomarker peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Detecting the amount of a biomarker peptide or polypeptide may comprise the steps of (a) contacting the peptide with a specific ligand, (b) (optionally) removing non-bound ligand, (c) measuring the amount of bound ligand. The bound ligand will generate an intensity signal. Binding according to the present disclosure includes both covalent and non-covalent binding. A ligand according to the present disclosure can be any compound, e.g., a peptide, polypeptide, nucleic acid, or small molecule, binding to the peptide or polypeptide described herein. Exemplary ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab).sub.2 fragments that are capable of binding antigen or hapten.

The present disclosure also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. The ligand or agent binds specifically to the peptide or polypeptide. Specific binding according to the present disclosure means that the ligand or agent should not bind substantially to ("cross-react" with) another peptide, polypeptide or substance present in the sample to be analyzed. The specifically bound peptide or polypeptide should be bound with at least 3 times higher, and in some embodiments at least 10 times higher or even at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Said method may be semi-quantitative or quantitative. Suitable methods are described in the following.

First, binding of a ligand may be measured directly, e.g. by NMR or surface plasmon resonance. Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, the amount of substrate may be saturating. The substrate may also be labeled with a detectable label prior to the reaction. For example, the sample is contacted with the substrate for an adequate period of time. An adequate period of time refers to the time necessary for a detectable, and in some embodiments measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.).

The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag may be at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include .sup.35S, .sup.125I, .sup.32P, .sup.33P and the like. A radioactive label can be detected by any method known and appropriate, e.g. a light-sensitive film or a phosphor imager. Suitable measurement methods according the present disclosure also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other detection methods as described above.

According to embodiments of the instant disclosure, the amount of a peptide or polypeptide may be detected as follows: (a) contacting a solid support comprising a ligand for the peptide or polypeptide as specified above with a sample comprising the peptide or polypeptide and (b) measuring the amount peptide or polypeptide which is bound to the support. The ligand may be chosen from the group consisting of nucleic acids, peptides, polypeptides, antibodies and aptamers. In some embodiments, the ligand is present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the disclosure. Suitable methods for fixing/immobilizing said ligand are well known and include, but are not limited to ionic, hydrophobic, covalent interactions and the like. It is also contemplated to use "suspension arrays" as arrays according to the present disclosure (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

Reference Amounts

Reference amounts can be calculated for a cohort of subjects (i.e. subjects which are known to have CKD) based on the average or mean values for a given biomarker by applying standard statistically methods. In one embodiment, the reference is determined in a cohort of subjects suffering from CKD using multivariable Proportional Hazard (Cox) Regression analysis (Cox DR. Regression models and life tables. J R Stat Soc (B). 1972; 34(series B):187-220). Techniques and assays useful in this type of analysis are described in the Examples and Figures referenced therein.

The median values for the biomarker(s) determined in a cohort of patients may be also used as a basis for establishing reference levels In certain embodiments, the term "reference level" herein refers to a predetermined value. In this context "level" encompasses the absolute amount, the relative amount or concentration as well as any value or parameter which correlates thereto or can be derived therefrom. As the skilled artisan will appreciate the reference level is predetermined and set to meet routine requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90%, 95% or 98%, respectively. These requirements may also be defined in terms of positive or negative predictive values. Nonetheless, based on the teaching given in the present invention it will always be possible for a skilled artisan to arrive at the reference level meeting those requirements. In one embodiment the reference level is determined in reference samples from healthy individuals. The reference level in one embodiment has been predetermined in reference samples from the disease entity to which the patient belongs. In certain embodiments the reference level can e.g. be set to any percentage between 25% and 75% of the overall distribution of the values in a disease entity investigated. In other embodiments the reference level can e.g. be set to the median, tertiles or quartiles as determined from the overall distribution of the values in reference samples from a disease entity investigated.

In one embodiment the reference level is set to the median value as determined from the overall distribution of the values in a disease entity investigated. The reference level may vary depending on various physiological parameters such as age, gender or subpopulation, as well as on the means used for the determination of the biomarker Y referred to herein. In one embodiment, the reference sample is from essentially the same type of cells, tissue, organ or body fluid source as the sample from the individual or patient subjected to the method of the invention, e.g. if according to the invention blood is used as a sample to determine the level of biomarker Y in the individual, the reference level is also determined in blood or a part thereof.

In certain embodiments, the term "at the reference level" refers to a level of the biomarker in the sample from the individual or patient that is essentially identical to the reference level or to a level that differs from the reference level by up to 1%, up to 2%, up to 3%, up to 4%, up to 5%.

In certain embodiments, the term "greater than the reference level" refers to a level of the biomarker in the sample from the individual or patient above the reference level or to an overall increase of 5%, 10%, 20%, 25%, 30%, 40%, 50%, 60%, 70%, 80%, 85%, 90%, 95%, 100% or greater, determined by the methods described herein, as compared to the reference level. In certain embodiments, the term increase refers to the increase in biomarker level in the sample from the individual or patient wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the reference level, e.g. predetermined from a reference sample.

In certain embodiments, the term "decrease" or "below" herein refers to a level of the biomarker in the sample from the individual or patient below the reference level or to an overall reduction of 5%, 10%, 20%, 25%, 30%, 40%, 50%, 60%, 70%, 80%, 85%, 90%, 95%, 96%, 97%, 98%, 99% or greater, determined by the methods described herein, as compared to the reference level. In certain embodiments, the term decrease in biomarker level in the sample from the individual or patient wherein the decreased level is at most about 0.9-, 0.8-, 0.7-, 0.6-, 0.5-, 0.4-, 0.3-, 0.2-, 0.1-, 0.05-, or 0.01-fold of the reference level, e.g. predetermined from a reference sample, or lower.

Methods of Treatment

Some methods of the invention further comprise administering a pharmaceutical agent or composition for treating chronic kidney disease to a subject with an increased risk of disease progression. Such pharmaceutical agents include for example agents of the class of angiotensin covrting enzyme inhibitors (ACEi) or of the class of the angiotensin receptor blockers (ARBs). Additional pharmaceutical agents include those agents undergoing clinical trial studies with a regulatory agency, such as the FDA or EMA. Dosage regimens may be adjusted to provide the optimum desired response (e.g., a therapeutic response). For example, a dose may be administered, several divided doses may be administered over time or the dose may be proportionally reduced or increased as indicated by exigencies of the therapeutic situation.

A physician having ordinary skill in the art can readily determine and prescribe the effective amount of the pharmaceutical composition required. The effectiveness of a given dose or treatment regimen of the antagonist can be determined, for example, by assessing signs and symptoms in the patient using standard In yet another aspect, the invention provides, after the identification step, a method of determining whether to continue administering the pharmaceutical agent or composition to a subject diagnosed with CKD comprising measuring current status of the CKD disease via standard techniques, such as GFR.

EXAMPLES

Sample Collection
Patient Cohort Description

The following study utilizes patients and samples from the Clinical Phenotyping Resource and Biobank research core within the NIH sponsored George M. O'Brien Renal Center (C-PROBE) study, identified as NCT01016613 in clinicaltrials.gov.

C-Probe is an observational time prospective multicenter, actively enrolling study in which 221 patients has simultaneously recorded for clinical and demographic parameters, clinical chemistry analysis and longitudinal regular medical follow ups.

Clinical and biomarker data were available for 393 patients of this cohort. Outcome measured data and time to the outcome occurrence was available for 221 patients. CKD events were defined based on the existing outcome categories according to Table A (FIG. 3). Patient characteristics and summary statistics of this cohort are presented in Table B (FIG. 4).

Patient samples were assayed to evaluate the utility of several biomarkers to aid in assigning an increased likelihood of CKD progression and increase incidence of outcome to a patient diagnosed with CKD.

Samples obtained from each patient were analyzed by immunoassay to determine the level of each biomarker Immunoassays were operated in a sandwich assay format or, for NT-proBNP, using the Elecsys® proBNP platform (Elecsys 20.10 immunoanalyzer).

Assay

Concentrations of ApoH (cat. no. ab108814, Abcam, Cambridge, United Kingdom) and EGF (cat. no. DEG00, R&D Systems, Minneapolis, Minn., U.S.A.) were measured in duplicate in urine samples using commercial enzyme-linked immunosorbent assay kits according to the manufacturer's protocol. Urine samples were diluted respectively 16 fold and 150 fold. The Lower Limits of Quantification were determined and respectively set to 0.96 µg/ml and 4.5 µg/ml.

Concentrations of GDF-15 (cat. no. DGD150, R&D Systems, Minneapolis, Minn., U.S.A.) were measured in duplicate in EDTA-plasma samples using commercial enzyme-linked immunosorbent assay kits according to the manufacturer's protocol. Plasma samples were diluted 10 fold. The Lower Limit of Quantification was determined and set to 93.8 pg/ml.

Albumin concentrations (cat. no. 11970569216, Roche Diagnostics, Mannheim, Germany) and NT-proBNP (cat. no. 04842464190, Roche Diagnostics, Mannheim, Germany) were measured respectively in urine and in EDTA-plasma using commercial CE certified test kits following the manufacturer's instructions.

The following characteristics were evaluated:

Dynamic concentration range; Lower and upper limits of quantification; Matrix effects; Precision; Accuracy; Stability; Selectivity and specificity; Dilution parallelism; and Interfering agents.

Statistical Analysis
Time to Event Analysis

The association of each of the five biomarkers GDF-15, EGF, NT-proBNP, ApoH, and albumin to creatinine ratio (AUCR), and combinations thereof, with the risk of CKD events was conducted by multivariable Proportional Hazard (Cox) Regression. Quantitative covariates were reduced and scaled. Each biomarker was added on top of available clinical parameters (age, gender and eGFR levels at baseline, henceforth denoted as basal model). All possible biomarker combinations were fitted (on top of the basal model) and their respective predictive models compared. Summary statistics for each model are shown in FIGS. 1-2. (goodness of fit information criteria). AIC (Akaike Information Criterion) and BIC (Bayesian Information Criterion) are two measures of quality of a statistical model for a set of data, which represent the amount of information lost when a given model is used to represent the data. Thus, the smaller value the better. They deal with the trade-off of goodness of fit and the complexity of the model. BIC is a version of AIC adjusted for the number of parameters in the model; BIC therefore penalizes complex models (with larger number of predictors).

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

REFERENCES

1. Coresh J, Astor B C, Greene T, Eknoyan G, Levey A S. Prevalence of chronic kidney disease and decreased kidney function in the adult US population: Third National Health and Nutrition Examination Survey. Am J Kidney Dis. 2003 January; 41(1):1-12.
2. Xue J L, Eggers P W, Agodoa L Y, Foley R N, Collins A J. Longitudinal study of racial and ethnic differences in developing end-stage renal disease among aged medicare beneficiaries. J Am Soc Nephrol. 2007 April; 18(4):1299-306.
3. Keith D S, Nichols G A, Gullion C M, Brown J B, Smith D H. Longitudinal follow-up and outcomes among a population with chronic kidney disease in a large managed care organization. Archives of internal medicine. 2004 Mar. 22; 164(6):659-63.
4. Lindeman R D, Tobin J, Shock N W. Longitudinal studies on the rate of decline in renal function with age. Journal of the American Geriatrics Society. 1985 April; 33(4):278-85.
5. Hu B, Gadegbeku C, Lipkowitz M S, Rostand S, Lewis J, Wright J T, et al. Kidney function can improve in patients with hypertensive CKD. J Am Soc Nephrol. 2012 April; 23(4):706-13.
6. Li L, Astor B C, Lewis J, Hu B, Appel L J, Lipkowitz M S, et al. Longitudinal progression trajectory of GFR among patients with CKD. Am J Kidney Dis. 2012 April; 59(4):504-12.
7. Taal M W, Brenner B M. Renal risk scores: progress and prospects. Kidney international. 2008 June; 73(11):1216-9.
8. Taal M W, Brenner B M. Defining renal risk. Current opinion in nephrology and hypertension. 2007 November; 16(6):554-6.
9. Taal M W, Brenner B M. Predicting initiation and progression of chronic kidney disease: Developing renal risk scores. Kidney international. 2006 November; 70(10):1694-705.
10. Clark W F, Macnab J J, Sontrop J M, Jain A K, Moist L, Salvadori M, et al. Dipstick proteinuria as a screening strategy to identify rapid renal decline. J Am Soc Nephrol. 2011 September; 22(9):1729-36.
11. Hallan S I, Ritz E, Lydersen S, Romundstad S, Kvenild K, Orth S R. Combining GFR and albuminuria to classify CKD improves prediction of ESRD. J Am Soc Nephrol. 2009 May; 20(5):1069-77.
12. Halbesma N, Jansen D F, Heymans M W, Stolk R P, de Jong P E, Gansevoort R T. Development and validation of a general population renal risk score. Clin J Am Soc Nephrol. 2011 July; 6(7):1731-8.
13. Echouffo-Tcheugui J B, Kengne A P. Risk models to predict chronic kidney disease and its progression: a systematic review. PLoS medicine. 2012;9(11):e1001344.
14. O'Seaghdha C M, Hwang S J, Ho J E, Vasan R S, Levy D, Fox C S. Elevated Galectin-3 Precedes the Development of CKD. J Am Soc Nephrol. 2013 September; 24(9):1470-7.
15. O'Seaghdha C M, Hwang S J, Larson M G, Meigs J B, Vasan R S, Fox C S. Analysis of a Urinary Biomarker Panel for Incident Kidney Disease and Clinical Outcomes. J Am Soc Nephrol. 2013 Aug. 29.
16. Fox C S, Gona P, Larson M G, Selhub J, Tofler G, Hwang S J, et al. A multi-marker approach to predict incident CKD and microalbuminuria. J Am Soc Nephrol. 2010 December; 21(12):2143-9.
17. Formentini I, Bobadilla M, Haefliger C, Hartmann G, Loghman-Adham M, Mizrahi J, et al. Current drug development challenges in chronic kidney disease (CKD)—identification of individualized determinants of renal progression and premature cardiovascular disease (CVD). Nephrol Dial Transplant. 2012 October; 27 Suppl 3:iii81-8.
18. Austin W J, Bhalla V, Hernandez-Arce I, Isakson S R, Beede J, Clopton P, et al. Correlation and prognostic utility of B-type natriuretic peptide and its amino-terminal fragment in patients with chronic kidney disease. American journal of clinical pathology. 2006 October; 126(4):506-12.
19. Spanaus K S, Kronenberg F, Ritz E, Schlapbach R, Fliser D, Hersberger M, et al. B-type natriuretic peptide concentrations predict the progression of nondiabetic chronic kidney disease: the Mild-to-Moderate Kidney Disease Study. Clinical chemistry. 2007 July; 53(7):1264-72.
20. Sato Y. Diagnostic and prognostic property of NT-proBNP in patients with renal dysfunction. Journal of cardiology. 2013 June; 61(6):446-7.
21. Yasuda K, Kimura T, Sasaki K, Obi Y, Iio K, Yamato M, et al. Plasma B-type natriuretic peptide level predicts kidney prognosis in patients with predialysis chronic kidney disease. Nephrol Dial Transplant. 2012 October; 27(10):3885-91.
22. Desai A S, Toto R, Jarolim P, Uno H, Eckardt K U, Kewalramani R, et al. Association between cardiac biomarkers and the development of ESRD in patients with type 2 diabetes mellitus, anemia, and CKD. Am J Kidney Dis. 2011 November; 58(5):717-28.
23. Svensson M, Gorst-Rasmussen A, Schmidt E B, Jorgensen K A, Christensen J H. NT-pro-BNP is an independent predictor of mortality in patients with end-stage renal disease. Clinical nephrology. 2009 Aprril; 71(4):380-6.
24. Wang A Y, Lam C W, Yu C M, Wang M, Chan I H, Zhang Y, et al. N-terminal pro-brain natriuretic peptide: an independent risk predictor of cardiovascular congestion, mortality, and adverse cardiovascular outcomes in chronic peritoneal dialysis patients. J Am Soc Nephrol. 2007 January; 18(1):321-30.
25. Breit S N, Carrero J J, Tsai V W, Yagoutifam N, Luo W, Kuffner T, et al. Macrophage inhibitory cytokine-1 (MIC-1/GDF15) and mortality in end-stage renal disease. Nephrol Dial Transplant. 2012 January; 27(1):70-5.
26. Lajer M, Jorsal A, Tarnow L, Parving H H, Rossing P. Plasma growth differentiation factor-15 independently predicts all-cause and cardiovascular mortality as well as deterioration of kidney function in type 1 diabetic patients with nephropathy. Diabetes care. 2010 July; 33(7):1567-72.
27. Hellemons M E, Mazagova M, Gansevoort R T, Henning R H, de Zeeuw D, Bakker S J, et al. Growth-differentiation factor 15 predicts worsening of albuminuria in patients with type 2 diabetes. Diabetes care. 2012 November; 35(11):2340-6.
28. Ranieri E, Gesualdo L, Petrarulo F, Schena F P. Urinary I L-6/EGF ratio: a useful prognostic marker for the progression of renal damage in IgA nephropathy. Kidney international. 1996 December; 50(6):1990-2001.
29. Stangou M, Papagianni A, B antis C, Liakou H, Pliakos K, Giamalis P, et al. Detection of multiple cytokines in the urine of patients with focal necrotising glomerulonephritis may predict short and long term outcome of renal function. Cytokine. 2012 January; 57(1):120-6.
30. Stangou M, Alexopoulos E, Papagianni A, Pantzaki A, Bantis C, Dovas S, et al. Urinary levels of epidermal growth factor, interleukin-6 and monocyte chemoattractant protein-1 may act as predictor markers of renal function outcome in immunoglobulin A nephropathy. Nephrology (Carlton, Vic. 2009 September; 14(6):613-20.
31. Tones D D, Rossini M, Manno C, Mattace-Raso F, D'Altri C, Ranieri E, et al. The ratio of epidermal growth factor to monocyte chemotactic peptide-1 in the urine predicts renal prognosis in IgA nephropathy. Kidney international. 2008 February; 73(3):327-33.
32. Lapsley M, Flynn F V, Sansom P A. Beta 2-glycoprotein-1 (apolipoprotein H) excretion and renal tubular malfunction in diabetic patients without clinical proteinuria. Journal of clinical pathology. 1993 May; 46(5):465-9.
33. Flynn F V, Lapsley M, Sansom P A, Cohen S L. Urinary excretion of beta 2-glycoprotein-1 (apolipoprotein H) and other markers of tubular malfunction in "non-tubular" renal disease. Journal of clinical pathology. 1992 July; 45(7):561-7.
34. Lapsley M, Sansom P A, Marlow C T, Flynn F V, Norden A G. Beta 2-glycoprotein-1 (apolipoprotein H) excretion in chronic renal tubular disorders: comparison with other protein markers of tubular malfunction. Journal of clinical pathology. 1991 October; 44(10):812-6.
35. Flynn F V, Lapsley M, Sansom P A, Norden A G. Absence of increased urinary excretion of adenosine-deaminase-binding protein by patients with chronic renal tubular malfunction. Clinica chimica acta; international journal of clinical chemistry. 1991 Aug. 30; 200(2-3):183-9.
36. Norden A G, Fulcher L M, Lapsley M, Flynn F V. Excretion of beta 2-glycoprotein I (apolipoprotein H) in renal tubular disease. Clinical chemistry. 1991 January; 37(1):74-7.

We claim:

1. A method for treating a subject suffering from chronic kidney disease, the method comprising:
   a) detecting an amount of EGF, albumin to creatinine ratio (AUCR), and one, two, or three additional biomarkers selected from the group consisting of GDF-15, NT-proBNP, glomerular filtration rate (GFR), and ApoH in a urine sample of the subject; and
   b) treating the subject with a pharmaceutical agent for chronic kidney disease when the amount of said biomarkers is altered relative to a reference amount that is indicative of increased risk for disease progression.

2. The method of claim 1, wherein said pharmaceutical agent is an angiotensin converting enzyme inhibitor.

3. The method of claim 1, wherein said pharmaceutical agent is an angiotensin receptor blocker.

4. The method of claim 1, further comprising the step c) monitoring status of CKD disease to determine whether to continue administering said pharmaceutical agent.

5. The method of claim 1, wherein the detecting comprises contacting, in vitro, the sample with a combination of detection agents, each agent having specific binding affinity for one of the biomarkers.

6. The method of claim 5, wherein the agent is an antibody or fragment thereof.

* * * * *

UNITED STATES PATENT AND TRADEMARK OFFICE
CERTIFICATE OF CORRECTION

PATENT NO. : 10,274,502 B2  
APPLICATION NO. : 15/034338  
DATED : April 30, 2019  
INVENTOR(S) : Maria Bobadilla et al.

Page 1 of 1

It is certified that error appears in the above-identified patent and that said Letters Patent is hereby corrected as shown below:

On the Title Page

Item [72], should read:
Maria Bobadilla, Rosenau (FR); Laura Badi, Basel (CH); Guillemette Duchateau-Nguyen, Riedisheim (FR); Laurent Essioux, Attenschwiller (FR); Hanno Langen, Loerrach (DE); Maria Chiara Magnone, Basel (CH); Thomas Schindler, Loerrach (DE); Martina Thier, Basel (CH); Ivan Formentini, Basel (CH); Gonzalo Christian Duran Pacheco, Riehen (CH); Corinne Solier, Sierentz (FR); Matthias Kretzler, Ann Arbor, MI (US); Viji Nair, Ann Arbor, MI (US); Wenjun Ju, Ann Arbor, MI (US)

Signed and Sealed this  
Thirty-first Day of December, 2019

Andrei Iancu  
*Director of the United States Patent and Trademark Office*

SEQUENCE LISTING

```
<160> NUMBER OF SEQ ID NOS: 5

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255
```

```
Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
            275                 280                 285

Asp Thr Gly Val Ser Leu Gln Thr Tyr Asp Asp Leu Leu Ala Lys Asp
        290                 295                 300

Cys His Cys Ile
305

<210> SEQ ID NO 2
<211> LENGTH: 1207
<212> TYPE: PRT
<213> ORGANISM: Homo sapiens

<400> SEQUENCE: 2

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
    210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
            260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
    290                 295                 300

Lys Ala Glu Asp Asp Thr Trp Glu Pro Glu Gln Lys Leu Cys Lys Leu
305                 310                 315                 320
```

-continued

```
Arg Lys Gly Asn Cys Ser Ser Thr Val Cys Gly Gln Asp Leu Gln Ser
            325                 330                 335

His Leu Cys Met Cys Ala Glu Gly Tyr Ala Leu Ser Arg Asp Arg Lys
        340                 345                 350

Tyr Cys Glu Asp Val Asn Glu Cys Ala Phe Trp Asn His Gly Cys Thr
            355                 360                 365

Leu Gly Cys Lys Asn Thr Pro Gly Ser Tyr Tyr Cys Thr Cys Pro Val
    370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
            420                 425                 430

Gly Lys Thr Cys Ser Gly Cys Ser Ser Pro Asp Asn Gly Gly Cys Ser
        435                 440                 445

Gln Leu Cys Val Pro Leu Ser Pro Val Ser Trp Glu Cys Asp Cys Phe
    450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
            500                 505                 510

Met Val Tyr Ala Leu Asp His Asp Pro Val Glu Asn Lys Ile Tyr Phe
        515                 520                 525

Ala His Thr Ala Leu Lys Trp Ile Glu Arg Ala Asn Met Asp Gly Ser
    530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
            580                 585                 590

Thr Lys Glu Asn Ile Ser Gln Pro Arg Gly Ile Ala Val His Pro Met
        595                 600                 605

Ala Lys Arg Leu Phe Trp Thr Asp Thr Gly Ile Asn Pro Arg Ile Glu
    610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
            660                 665                 670

Gly Ser Lys Arg Arg Arg Leu Thr Gln Asn Asp Val Gly His Pro Phe
        675                 680                 685

Ala Val Ala Val Phe Glu Asp Tyr Val Trp Phe Ser Asp Trp Ala Met
    690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val Val His Pro
                725                 730                 735
```

```
Leu Ala Lys Pro Gly Ala Asp Pro Cys Leu Tyr Gln Asn Gly Gly Cys
            740                 745                 750

Glu His Ile Cys Lys Lys Arg Leu Gly Thr Ala Trp Cys Ser Cys Arg
            755                 760                 765

Glu Gly Phe Met Lys Ala Ser Asp Gly Lys Thr Cys Leu Ala Leu Asp
            770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
            820                 825                 830

Asp Asp Cys Ala Pro Val Gly Cys Ser Met Tyr Ala Arg Cys Ile Ser
            835                 840                 845

Glu Gly Glu Asp Ala Thr Cys Gln Cys Leu Lys Gly Phe Ala Gly Asp
            850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
            900                 905                 910

Ile Asp Glu Cys Gln Leu Gly Glu His Ser Cys Gly Glu Asn Ala Ser
            915                 920                 925

Cys Thr Asn Thr Glu Gly Gly Tyr Thr Cys Met Cys Ala Gly Arg Leu
            930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
                965                 970                 975

Pro Leu Ser His Asp Gly Tyr Cys Leu His Asp Gly Val Cys Met Tyr
            980                 985                 990

Ile Glu Ala Leu Asp Lys Tyr Ala Cys Asn Cys Val Val Gly Tyr Ile
            995                 1000                1005

Gly Glu Arg Cys Gln Tyr Arg Asp Leu Lys Trp Trp Glu Leu Arg
        1010                1015                1020

His Ala Gly His Gly Gln Gln Gln Lys Val Ile Val Val Ala Val
        1025                1030                1035

Cys Val Val Val Leu Val Met Leu Leu Leu Leu Ser Leu Trp Gly
        1040                1045                1050

Ala His Tyr Tyr Arg Thr Gln Lys Leu Leu Ser Lys Asn Pro Lys
        1055                1060                1065

Asn Pro Tyr Glu Glu Ser Ser Arg Asp Val Arg Ser Arg Arg Pro
        1070                1075                1080

Ala Asp Thr Glu Asp Gly Met Ser Ser Cys Pro Gln Pro Trp Phe
        1085                1090                1095

Val Val Ile Lys Glu His Gln Asp Leu Lys Asn Gly Gly Gln Pro
        1100                1105                1110

Val Ala Gly Glu Asp Gly Gln Ala Ala Asp Gly Ser Met Gln Pro
        1115                1120                1125

Thr Ser Trp Arg Gln Glu Pro Gln Leu Cys Gly Met Gly Thr Glu
        1130                1135                1140

Gln Gly Cys Trp Ile Pro Val Ser Ser Asp Lys Gly Ser Cys Pro
```

```
                     1145                1150                1155

Gln Val Met Glu Arg Ser Phe His Met Pro Ser Tyr Gly Thr Gln
         1160                1165                1170

Thr Leu Glu Gly Gly Val Glu Lys Pro His Ser Leu Leu Ser Ala
     1175                1180                1185

Asn Pro Leu Trp Gln Gln Arg Ala Leu Asp Pro Pro His Gln Met
     1190                1195                1200

Glu Leu Thr Gln
     1205

<210> SEQ ID NO 3
<211> LENGTH: 134
<212> TYPE: PRT
<213> ORGANISM: Homo sapiens

<400> SEQUENCE: 3

Met Asp Pro Gln Thr Ala Pro Ser Arg Ala Leu Leu Leu Leu Phe
1               5                   10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
        130

<210> SEQ ID NO 4
<211> LENGTH: 345
<212> TYPE: PRT
<213> ORGANISM: Homo sapiens

<400> SEQUENCE: 4

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
                20                  25                  30

Thr Val Val Pro Leu Lys Thr Phe Tyr Glu Pro Gly Glu Glu Ile Thr
            35                  40                  45

Tyr Ser Cys Lys Pro Gly Tyr Val Ser Arg Gly Gly Met Arg Lys Phe
        50                  55                  60

Ile Cys Pro Leu Thr Gly Leu Trp Pro Ile Asn Thr Leu Lys Cys Thr
65                  70                  75                  80

Pro Arg Val Cys Pro Phe Ala Gly Ile Leu Glu Asn Gly Ala Val Arg
                85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
```

```
            115                 120                 125
Lys Trp Ser Pro Glu Leu Pro Val Cys Ala Pro Ile Ile Cys Pro Pro
    130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
        195                 200                 205

Ser Arg Pro Asp Asn Gly Phe Val Asn Tyr Pro Ala Lys Pro Thr Leu
    210                 215                 220

Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
                245                 250                 255

Met Pro Ser Cys Lys Ala Ser Cys Lys Val Pro Val Lys Lys Ala Thr
            260                 265                 270

Val Val Tyr Gln Gly Glu Arg Val Lys Ile Gln Glu Lys Phe Lys Asn
        275                 280                 285

Gly Met Leu His Gly Asp Lys Val Ser Phe Phe Cys Lys Asn Lys Glu
    290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                325                 330                 335

Thr Asp Ala Ser Asp Val Lys Pro Cys
            340                 345

<210> SEQ ID NO 5
<211> LENGTH: 609
<212> TYPE: PRT
<213> ORGANISM: Homo sapiens

<400> SEQUENCE: 5

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140
```

```
Asp Val Met Cys Thr Ala Phe His Asp Asn Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
```

```
                        565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu
```